United States Patent [19]

Woo

[11] 4,446,123

[45] May 1, 1984

[54] PROCESS OF RADIOIMAGING THE MYOCARDIUM OF MAMMALS UTILIZING RADIOLABELED LIPOPHILIC CATIONS

[75] Inventor: David V. Woo, Downingtown, Pa.

[73] Assignee: Hahnemann University, Philadelphia, Pa.

[21] Appl. No.: 433,871

[22] Filed: Oct. 13, 1982

[51] Int. Cl.³ .................... A61K 43/00; A61K 49/00
[52] U.S. Cl. .................................... 424/1.1; 424/9; 564/289; 260/440; 568/9
[58] Field of Search ................ 424/1.1, 9; 260/440; 564/289; 568/9

[56] References Cited

U.S. PATENT DOCUMENTS 4,107,283 8/1978 Pratt et al. ........................... 424/1
4,387,087 6/1983 Deutsch ............................... 424/1

Primary Examiner—Christine M. Nucker
Attorney, Agent, or Firm—Paul & Paul

[57] ABSTRACT

Process of radioimaging the myocardium of mammals using intravenous injection of radiolabeled lipophilic cations of quaternary ammonium, quaternary phosphonium or quaternary arsonium compounds of the formula

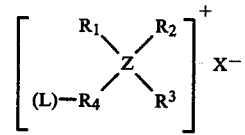

where $R_1$ and $R_2$ are alkyl or aryl groups, $R_3$ and $R_4$ are phenyl or benzyl groups, X is $Br^-$, $I^-$ or $Cl^-$, L is $I^{123}$, $I^{125}$, $I^{131}$, $Br^{77}$, $Br^{82}$ or $F^{18}$ and Z is nitrogen, phosphorous or arsenic.

18 Claims, No Drawings

PROCESS OF RADIOIMAGING THE MYOCARDIUM OF MAMMALS UTILIZING RADIOLABELED LIPOPHILIC CATIONS

BACKGROUND OF THE INVENTION

Radiolabeled myocardial imaging agents have been known for several years but the diagnostic use of such agents has been severely limited by the fact that other tissues or fibers in the general vicinity of the myocardium have sufficiently high take-up values of such agents to interfere with the myocardium radioimage. The principal interfering tissues are the blood, lung and liver.

SUMMARY OF THE INVENTION

The present invention relates broadly to a process for radioimaging the myocardium of mammals by first preferentially concentrating a radiolabeled lipophilic cation in the myocardial fibers and then producing a radioimage using known radioimaging techniques.

In carrying out the step of preferentially concentrating such a radiolabeled cation in myocardial fibers I have found that there is a class of agents capable of accomplishing this which class broadly comprises radiolabeled lipophilic cations of quaternary ammonium, quaternary phosphonium or quaternary arsonium compounds having at least two aryl groups.

I have discovered a class of substances which do in fact exhibit a surprising preference for myocardial fibers when injected intravenously into mammals. In fact the myocardial preference of these substances is sufficiently great to provide high myocardial concentration of radioactivity and likewise myocardial/non-target ratios great enough to provide substantially improved diagnostic imaging of the myocardium.

Radiolabeled quaternary ammonium, quaternary phosphonium or quaternary arsonium compounds are injected intravenously as hereinafter described. This results in the preferential uptake in the myocardium of the radiolabeled cation as described above.

A radioimage of the myocardium is then taken.

The class of compounds having the desired myocardial preference characteristics is made up of quaternary ammonium, quaternary phosphonium and quaternary arsonium halides having at least two aryl groups selected from the class comprising phenyl and benzyl groups. Examples of such compounds are:

Tetraphenylammonium bromide
Tetrabenzylammonium bromide
Tetraphenylphosphonium bromide
Tetrabenzylphosphonium bromide
Tetraphenylarsonium bromide
Diphenyldimethylammonium bromide
Phenylbenzyldimethylammonium bromide
Dibenzyldimethylammonium bromide
Diphenyldimethylphosphonium bromide
Phenylbenzyldimethylphosphonium bromide
Dibenzyldimethylphosphonium bromide.

In the above list of quaternary compounds the methyl groups may be replaced with ethyl and/or propyl groups and the bromine may be replaced by other halides such as iodine or chlorine.

In order to impart radioimaging characteristics to the above quaternary compounds and to thus produce the materials used in the practice of the present invention radioactive labels are affixed in known ways to one or more of the aryl groups. Such labels may be selected from the following elements: $I^{123}$, $I^{125}$, $I^{131}$, $Br^{77}$, $Br^{82}$ and $F_{18}$.

STATEMENT OF PRIOR ART

The application of radioiodine to the labeling of organic compounds for use in diagnostic nuclear medicine is well documented. Other radioactive chemicals have been used as well. Specifically for commercial use in heart imaging, radioactive thallium has been employed almost exclusively. The use of thallium has been described by Lebowitz, E. et al., J. Nucl. Med. 16:2, 151 (1975). However, the use of thallium is expensive. It also results in poor imaging and vague interpretation. This is due to several inadequacies of thallium such as the low gamma emissions of thallium.

Therefore, there has been increasing interest in finding compounds which will lead to higher quality imaging. New labeled compounds are also sought which would highly localize in the heart with respect to the neighboring organs such as the blood, lungs and liver which otherwise interfere with or obstruct the image of the heart. Finally, a new compound is sought which would have a heart uptake greater than that of thallium so as to produce a stronger, clearer image.

There exists a group of compounds called radiolabeled lipophilic cations. These compounds have been used extensively to study active transport in a variety of bacterial and mammalian cell systems.

Radiolabeled lipophilic cations have been applied not as a heart imaging agent, but as a biochemical method to evaluate the state of the transmembrane potential by virtue of their ability to penetrate the hydrophobic core of the membrane. These ions have a unique propensity for charge decentralization which enables passive equilibration with the electrical potential across the membrane. First introduced by Skulachev, Curr. Top. Bioenerg. 4,127–190 (1971), this method has been extensively used in numerous biological systems as described by Kamo et al., J. Memb. Biol. 49, 105–121 (1979), Hirata et al., Proc. Natl. Acad. Sci. USA 70, 1804–1808 (1973) and Lichtshtein et al., Proc. Natl. Acad. Sci., USA 76, 650–654 (1979).

It is theorized that if radiolabeled lipophilic cations of quaternary ammonium, quaternary phosphonium and quaternary arsonium compounds have at least two aryl groups, the charge of the cations will sufficiently decentralize to enable localization of the cation in the myocardium according to the relatively high net negative potential known to exist across myocardial membranes.

The compounds of the subject invention are chemically distinct from any biochemical marker that has been applied to myocardial imaging. These compounds exhibit high myocardial concentration of radioactivity and favorable ratios of myocardial concentration to blood, liver and lung concentration ratios. In addition, the myocardial concentration of radioactivity appears to be constant with time while other major organs show declining levels of radioactivity, leading to even greater target to nontarget ratios of concentration.

Counsell et al., J. Nucl. Med. 15:11, pp. 991–996 (1974), described studies in animals using radioiodinated bretylium analogs for myocardial scanning. These compounds contain only one aryl group. Consequently, the myocardial concentration of radioactivity relative to nontarget tissue concentration of radioactivity was found to be significantly lower in heart/blood than thallium and comparable to thallium in heart/lung and heart/liver ratios. Furthermore, the total myocardial uptake of the radioactivity is much lower than that produced by the subject invention.

DETAILED DESCRIPTION OF THE INVENTION

The present invention is directed to radiolabeled lipophilic cations of quaternary ammonium, quaternary phosphonium and quaternary arsonium compounds of the formula

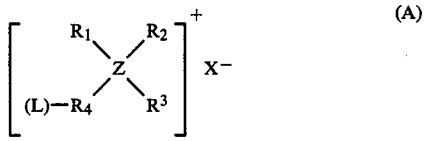

where $R_1$ and $R_2$ are the same or different and are alkyl or aryl groups, $R_3$ and $R_4$ are the same or different and are phenyl or benzyl groups, X is $Br^-$, $I^-$ or $Cl^-$, L is gamma-emitting $^{123}I$, $^{125}I$, $^{131}I$, $^{77}Br$, $^{82}Br$ or $^{18}F$ and Z is nitrogen, phosphorous or arsenic.

The radiolabeled lipophilic cations of formula A demonstrate a marked superiority in charge decentralization (or delocalization) in comparison to radioactive thallium which, as mentioned above, has been described in the art by Lebowitz, E. et al., J. Nucl. Med. 16:2, 151 (1975), as a heart imaging agent. This charge decentralization enables passive equilibration with the electrical potential across the membrane. Consequently, these radiolabeled lipophilic cations of formula A localize in the myocardium according to the relatively high net negative resting potential known to exist across myocardial membranes.

In tests on rats the radiolabeled lipophilic cations of formula A show rapid accumulation and significant localization in the heart. In other words, the ratio of the concentration of radioactivity in the heart to the concentration of the radioactivity in the non-target areas such as the blood, lungs and liver is high. In addition, the myocardial concentration of radioactivity appears to be constant with time while other major organs show declining levels of radioactivity. This significant localization in the heart is a distinct advantage of the radioiodinated cations of formula A.

As utilized herein, the term "alkyl" indicates either methyl, ethyl, n-propyl or i-propyl. The term "aryl" as utilized herein means either phenyl or benzyl. The term "iodo" indicates all radioisotopes of iodine. In formula A, (L) can be ortho, meta or para to the quaternary group, with para being preferred.

There are limitations on the possible compounds that may be used in the process of this invention. A minimum of two aryl groups are required so that the compound should not be too polar and thus be washed away by the biological system. Conversely, the size and number of substituent groups of the compound is limited by the need for solubility of these compounds.

Preferred compounds in accordance with the present invention include iodotetraphenylphosphonium bromide, iodomethyltriphenylphosphonium bromide, iodophenylbenzyldimethylammonium bromide, iodotetraphenylarsonium chloride, iodobenzyltriphenylphosphonium bromide, bromobenzyltriphenylphosphonium bromide, iodobenzyltriphenylphosphonium chloride, iododibenzyldimethylammonium bromide.

As stated above, the radioactive lipophilic cations of formula A rapidly localize and persist in the heart following intravenous administration. In tests on rats, the compounds of the invention showed a high accumulation in the heart during a time span of 15 minutes to two hours. The concentration of the compounds of the invention in the heart, called heart uptake, during this time span is much higher than for any other chemical that has been used for heart imaging. Additionally, over this time span, the concentration of the compounds of the invention declines in the neighboring, nontarget organs.

The radioiodinated compounds of the subject invention may be administered in an aqueous or an aqueous/alcoholic medium.

The compounds of this invention are commercially available or may be produced by a process that anyone skilled in the art can determine. The following examples illustrate the invention. Other compounds of these types may be produced with different substituent groups by methods which would be apparent to one skilled in the art. Further, each of the substituent configurations may surround either an ammonium, a phosphonium or an arsonium complex.

EXAMPLE 1

0.005 ml of N,N-Dimethylaniline was dissolved in 0.100 ml of methanol containing approximately 0.5 mCi of sodium [$^{125}I$]-iodide. 0.020 ml of a freshly prepared solution of chloramine-T in methanol (0.001 gm/0.001 ml) was added and the solution was mixed thoroughly for five minutes. 0.100 ml of a saturated solution of sodium metabisulfite was added and the solution was again mixed thoroughly.

The reaction mixture was applied to a high performance liquid chromatographic column (Waters Associates RCM-100 $C_{18}$-reverse phase column) and the intermediate product was eluted with methanol:water (7:3 V:V). Iodo-(N,N) dimethylaniline has a capacity factor $k'$ ($k'$=(Volume at which product elutes-void volume)÷(void volume)) of 7.8 while the $k'$ for N,N-dimethylaniline is 3.5.

p-Iodo-N,N-dimethylaniline was extracted from the methanol:water mixture with a small amount of chloroform after which the chloroform was dried with magnesium sulfate and 0.050 ml of benzyl bromide was added. The mixture was stirred overnight, extracted twice with saline, passed through a 0.22 μM Millipore filter, and stored in a stoppered serum bottle at 5° C.

The radiochemical purity of the final product, p-Iodophenylbenzyldimethylammonium bromide, was verified by thin layer chromatography. The $R_f$ valve for the product was 0.35 in acetone: water (4:1 V:V). Greater than 95% of the assayed activity was associated with the product, resulting in an overall radiochemical yield of approximately 72%. An aliquot was used for determination at specific activity using the method described by Burns, H. D. et al., J. Nucl. Med. 21:875–879 (1980). The measured specific activity was at least 40 Ci/mmole.

EXAMPLE 2

Tritiated tetraphenylphosphonium bromide is commercially available. Besides tritium, this compound may be labeled with other known markers such as a radioisotope of iodine. For example, by standard processes such as a radioactive iodine exchange reaction using commercially available radioactive sodium iodide and iodotetraphenylphosphonium bromide may be produced. The iodotetraphenylphosphonium bromide may be synthesized by the process described by Horner, L. and Hoffman, H., Chem. Ber. 91:45 (1957). However, iodination has not yet been accomplished.

EXAMPLE 3

Tritiated methyltriphenylphosphonium bromide is commercially available. Radiohalogenation of this compound may be carried out by halogen exchange. However, iodinated methyltriphenylphosphonium was not found to be water soluble as was the tritiated compound.

EXAMPLE 4

I*-iodobenzylphenylphosphonium bromide where I* is $^{125}$I, $^{123}$I or $^{131}$I may potentially be synthesized from p-nitrobenzyltriphenylphosphonium bromide via the triazene approach of Tewson, T. J. and Welch, M. J., J. Nucl. Med. 20,671 (1979) and Maeda, W., Tewson, T. J. and Welch, M. J., Third International Symposium on Radiopharmaceutical Chemistry, June 16–20, 1980.

Five grams of p-nitrobenzyltriphenylphosphonium bromide was dissolved in about 150 ml of methanol. This solution was transferred into a Parr hydrogenation bottle. About one gram of Raney nickel that has been previously washed with absolute ethanol was added to this solution. The Parr hydrogenation bottle was placed into the Parr hydrogenation apparatus. A vacuum was then pulled on the entire apparatus and followed by a purge with hydrogen gas. This was repeated a minimum of three times. The vacuum was of long enough duration to allow the gas in the methanol to bubble out.

After the final purge, hydrogen was allowed to enter at a pressure of 70 psi. The reaction proceeded for at least 24 hours while maintaining the hydrogen pressure at 70 psi. After reaction, the bottle was removed from the device and the filter suctioned carefully off the solvent with careful addition of more solvent to keep the nickel wet. The nickel-containing funnel was placed into dilute nitric acid immediately! Then the methanol solvent was evaporated off in Rotovap and further dried in vacuum overnight. An NMR spectrum of this product was consistent with the structure of p-NH$_2$benzyltriphenylphosphonium bromide. Via a Sandmeyer reaction on the triazene approach of Tewson mentioned above, this product may be converted to I*-iodobenzyltriphenylphosphonium bromide.

EXAMPLE 5

A 2:1 excess of p-bromobenzylbromide dissolved in 20–30 ml of degassed (argon) toluene is added to 2.62 grams of triphenylphosphine dissolved in 10 ml of degassed toluene. The reaction mixture was heated to reflux overnight in an oil bath. The phosphonium salt, p-bromobenzyltriphenylphosphonium bromide, precipitated out of solution. Radioactive labeling has not yet been performed.

EXAMPLE 6

A 2:1 excess of o-iodobenzylchloride dissolved in degassed (argon) toluene was added to a degassed solution of 5.18 gm of triphenylphosphine dissolved in 100 ml of toluene. The reaction mixture was heated to reflux (about 110° C.) for 66 hours. The product precipitated out of solution during the course of the reaction.

After allowing the reaction mixture to cool, to ambient temperature, about 30 ml of pet ether was added to the mixture. The precipitate was filtered off and washed with copious amounts of pet ether. The final wash was with ethyl ether. The product was o-iodobenzyltriphenylphosphonium chloride.

Radioactive labeling has not yet been performed.

EXAMPLE 7

Dibenzyldimethylammonium was documented for use in mitochondrial membrane penetration by Bakeeva, L. E. et al., Biochem. Biophys. Acta, 216 (1970) 13–21. The accumulation of dibenzyldimethylammonium in response to an electrical gradient was later studied by Altendorf et al., J. Bio. Chem. 250:4, 1403–1412 (1975). By standard processes, this known compound may be labeled with a radioactive halogen to form a compound such as I-125-iododibenzyldimethylammonium bromide.

EXAMPLE 8

Higuti, T. et al., J. Biol. Chem. 255:16, 7631–7636 (1980), noted that tetraphenylarsonium chloride may be obtained commercially. This compound may be labeled with a radioactive halogen by standard methods as discussed in Example 2 to form compounds such as I-125-iodotetraphenylarsonium chloride. If the tetraphenylarsonium compound is made with radioactive arsenic, halogen labeling may be unnecessary.

EXAMPLE 9

Bioassays were performed using compounds from the foregoing examples. Specifically, I-125-iodophenylbenzyldimethylammonium bromide synthesized in accordance with the method described in Example 1, H-3-tetraphenylphosphonium bromide as described in Example 2 and H-3-methyltriphenylphosphonium bromide as described in Example 3 were tested. The compounds were prepared for injection by pipetting 0.400 ml of the compound in ethanol (0.250 mCi/0.5 ml) into 4.00 ml of 0.9% saline solution. This solution was assayed by diluting 0.100 ml of the compound up to 10 ml (saline), pipetting 0.020 ml into cooling vials and adding 10 ml of scintillation cocktail (NEN Aquasol II).

Twelve female Sprague-Dawley rats (about 220 grams), non-fasted, were lightly etherized and administered 0.2 ml solution of about 0.010 mCi of the compound (10 mCi/mg) in tail vein. At 15 minutes, 30, 60 and 120 minutes after administering the injection, groups of three animals were sacrificed by CO$_2$ overdose inhalation. Selected tissues were removed (50–80 mg) and placed into preweighed scintillation vials. The organs sampled were blood, brain, heart (apex), lungs, liver, spleen, pancreas, stomach, small intestine, and kidney, and muscle. After re-weighing the sample vials, the tissues were processed for liquid scintillation counting.

The concentration of activity in the heart and neighboring organs was calculated as a percent of administered dose per gram. The ratio of the concentration of activity in the heart to the concentration of activity in the nontarget organs was then calculated. The results are reported in the following table.

The compounds of the subject invention that were tested resulted in much more favorable heart imaging characteristics than the presently used thallium or even the bretyllium analogs suggested by Counsell, R. E. et al., J. Nucl. Med. 15 #11, 991–996 (1974). The table below shows that the heart uptake of the compounds of the subject invention is much greater than either thallium or the bretyllium analog. The target to nontarget ratios of the compounds of the subject invention are also much greater than those presented by thallium.

TABLE I

Distribution of Radioactivity in Rats after Administration of Heart Imaging Agent

| Labeled Compound Corresponding to Example No. | Percent Dose/Gram | | | | Ratio | | | Time After Administration |
|---|---|---|---|---|---|---|---|---|
| | BLOOD | LUNG | LIVER | HEART | HEART/BLOOD | HEART/LUNG | HEART/LIVER | |
| 1 | 0.257 | 1.224 | 0.709 | 6.438 | 25.19 | 5.28 | 9.27 | 15 MIN. |
| 2* | 0.048 | 1.407 | 0.387 | 4.100 | 87.2 | 2.91 | 10.73 | |
| 3* | 0.067 | 1.036 | 0.280 | 3.559 | 53.4 | 3.4 | 13.9 | |
| 1 | 0.259 | 1.279 | 0.556 | 6.700 | 25.91 | 5.43 | 12.15 | 30 MIN. |
| 2 | 0.036 | 1.316 | 0.485 | 4.407 | 123.9 | 3.4 | 9.2 | |
| 3 | 0.055 | 1.116 | 0.228 | 3.466 | 61.6 | 3.1 | 15.5 | |
| 1 | 0.173 | 0.676 | 0.374 | 5.919 | 35.61 | 8.89 | 16.36 | 60 MIN. |
| 2 | 0.014 | 0.993 | 0.364 | 4.257 | 306.5 | 4.4 | 16.6 | |
| 3 | 0.043 | 0.709 | 0.087 | 3.021 | 71.2 | 4.3 | 30.1 | |
| 1 | 0.149 | 0.436 | 0.410 | 6.860 | 49.03 | 15.56 | 14.55 | 120 MIN. |
| 2 | 0.012 | 0.705 | 0.224 | 4.170 | 416.6 | 5.9 | 19.8 | |
| 3 | 0.041 | 0.558 | 0.064 | 2.468 | 60.1 | 4.4 | 39.8 | |
| R IBA+ | 0.02 | 0.128 | 0.112 | 0.832 | 41.5 | 6.5 | 7.5 | |

*Labeled with tritium
+Radioiodonated Bretyllium Analog. Figures reported by Counsell, R. E. et al., J. Nucl. Med. 15:11, 991–996 (1974). Individual organ concentrations were reported by Counsell, et al. as percent administered (kg.) dose/gm. They were converted to the same form as the other results by dividing by the assumed average mass of a rat of 0.25 kg. The concentration in the heart is the ventricle concentration.

In a separate test, I-125-iodophenylbenzyldimethylammonium bromide of the subject invention was compared to thallium, which is the state of the art heart imaging agent. Results are displayed in the following table. The results were obtained 30 minutes after administration of the heart imaging agent.

TABLE 2

Radioactivity Distribution in Rats after Administration of I-PBDA vs. Thallium

| | Percent Dose/Gram | | | | Ratio | | |
|---|---|---|---|---|---|---|---|
| | BLOOD | LUNG | LIVER | HEART | HEART/BLOOD | HEART/LUNG | HEART/LIVER |
| I-phenylbenzyl-dimethylammonium bromide | 0.1133 | 0.9472 | 0.3456 | 4.6213 | 42.08 | 5.04 | 13.33 |
| Thallium | 0.0431 | 1.515 | 1.2275 | 3.5858 | 100.43 | 2.44 | 3.11 |

What is claimed is:

1. A process of imaging the myocardium of mammals consisting of intravenously injecting radiolabeled lipophilic cations of quaternary ammonium, quaternary phosphonium or quaternary arsonium compounds having the general formula

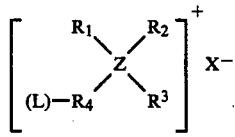

where $R_1$ and $R_2$ are alkyl or aryl groups, $R_3$ is a phenyl or benzyl group, $R_4$ is a radiolabelled phenyl or benzyl group and X is $Br^-$, $I^-$ or $Cl^-$ and where L is $I^{123}$, $I^{125}$, $I^{131}$, $Br^{77}$, $Br^{82}$ or $F^{18}$ and Z is nitrogen, phosphorous or arsenic, and then radioimaging the myocardium.

2. The process of claim 1 in which the quaternary compound is a Halotetraarylammonium halide.

3. The process of claim 1 in which the quaternary compound is a Halotetraarylphosphonium halide.

4. The process of claim 1 in which the quaternary compound is a Halotetraarylarsonium halide.

5. The process of claim 3 in which the quaternary compound is Iodotetraphenylphosphonium bromide.

6. The process of claim 4 in which the quaternary compound is Iodotetraphenylarsonium chloride.

7. The process of claim 3 in which the quaternary compound is Iodobenzyltriphenylphosphonium bromide.

8. The process of claim 3 in which the quaternary compound is Bromobenzyltriphenylphosphonium bromide.

9. The process of claim 3 in which the quaternary compound is Iodobenzyltriphenylphosphonium chloride.

10. The process of claim 1 in which the quaternary compound is a Halodiaryldialkylammonium halide.

11. The process of claim 1 in which the quaternary compound is a Halodiaryldialkylphosphonium halide.

12. The process of claim 1 in which the quaternary compound is a Halodiaryldialkylarsonium halide.

13. The process of claim 10 in which the quaternary compound is Iodobenzyldimethylammonium bromide.

14. The process of claim 10 in which the quaternary compound is a Iodophenylbenzyldimethylammonium bromide.

15. The process of claim 1 in which the quaternary compound is a Haloalkyltriarylammonium halide.

16. The process of claim 1 in which the quaternary compound is a Haloalkyltriarylphosphonium halide.

17. The process of claim 1 in which the quaternary compound is a Haloalkyltriarylarsonium halide.

18. The process of claim 15 in which the quaternary compound is Iodomethyltriphenylphosphonium bromide.

* * * * *